United States Patent [19]

Faler et al.

[11] Patent Number: 4,766,254

[45] Date of Patent: Aug. 23, 1988

[54] METHOD FOR MAXIMIZING YIELD AND PURITY OF BISPHENOL A

[75] Inventors: Gary R. Faler, Scotia, N.Y.; Michael J. Cipullo, Mt. Vernon, Ind.

[73] Assignee: General Electric Company, Schenectady, N.Y.

[21] Appl. No.: 104,602

[22] Filed: Oct. 5, 1987

[51] Int. Cl.$^4$ .............................................. C07C 37/68
[52] U.S. Cl. ..................................... 568/724; 568/748; 568/757
[58] Field of Search ............... 568/702, 703, 724, 748, 568/757

[56] References Cited

U.S. PATENT DOCUMENTS

| | | | |
|---|---|---|---|
| 3,234,290 | 2/1966 | Rocklin | 568/703 |
| 4,107,218 | 8/1978 | Konard et al. | 568/724 |
| 4,375,567 | 3/1983 | Faler et al. | 568/724 |
| 4,386,224 | 5/1983 | Deitman | 568/703 |

FOREIGN PATENT DOCUMENTS

| | | | |
|---|---|---|---|
| 2048661 | 4/1972 | Fed. Rep. of Germany | 568/724 |
| 0031486 | 3/1981 | Japan | 568/757 |
| 1022583 | 3/1984 | United Kingdom | 568/703 |
| 107876 | 3/1984 | U.S.S.R. | 568/703 |

*Primary Examiner*—Werren B. Lone
*Attorney, Agent, or Firm*—William H. Pittman; James C. Davids, Jr.; James Magee, Jr.

[57] ABSTRACT

Product losses and color formation are sometimes encountered in the synthesis of bisphenol A from phenol and acetone in the presence of a cation exchange resin, particularly in the crude product stream from which bisphenol A has been separated via its phenol adduct. Such losses are suppressed and the crude product stream stabilized and decolorized by contact with an anion exchange resin.

9 Claims, No Drawings

METHOD FOR MAXIMIZING YIELD AND PURITY OF BISPHENOL A

This invention relates to the preparation and purification of bisphenol A, and more particularly to the maximization of product yield.

Bisphenol A, or 2,2-bis(4-hydroxyphenyl)propane, is a valuable chemical intermediate for the production of various resinous materials, notably epoxy resins and polycarbonates. It is commercially produced by the acid-catalyzed condensation of phenol and acetone. A common method of preparation involves employing as the acid catalyst a sulfonated cation exchange resin in the free acid form, generally in combination with a mercaptan as a reaction rate accelerator.

The product stream from the reaction is frequently subjected to conditions whereby a solid adduct of bisphenol A and phenol is separated and subjected to further treatment to isolate a major proportion of the bisphenol A. There remains a liquid stream (hereinafter "mother liquor") containing crude bisphenol A in combination with various impurities, from which further bisphenol A is generally recovered by distillation. Typical distillation conditions include temperatures in the range of about 210°-220° C. and reduced pressure.

It is sometimes found that substantial product losses occur during this distillation step. Such losses may be as high as 15-40% of the total bisphenol A content of the mother liquor. Moreover, the mother liquor is frequently contaminated with darkly colored materials which are difficult or impossible to remove during bisphenol A purification. These situations obviously need correction, since product losses of this magnitude cannot be tolerated when a high rate of production is desired and highly colored product is unacceptable.

It has now been discovered that the loss of and color formation in bisphenol A are caused, at least in part, by acid-catalyzed cracking during the distillation step. Apparently, low molecular weight sulfonic acids are present in the cation exchange resin, are leached therefrom by the product stream and remain in the mother liquor. Upon heating of said mother liquor, these low molecular weight sulfonic acids, though present in very small proportions (e.g., about 200 ppm.), cause cracking of the product into phenol, isopropenylphenol and various oligomers and condensation products of the latter, including highly colored materials.

Accordingly, the present invention is a method for stabilizing a liquid crude bisphenol A product stream which comprises contacting it with a basic anion exchange resin at a temperature in the range of about 45°-125° C.

As previously mentioned, the liquid crude bisphenol A product stream treated by the method of this invention is ordinarily mother liquor from which a major proportion of the bisphenol A has previously been removed in the form of its adduct with phenol. Said mother liquor contains, in addition to bisphenol A, numerous impurities which are subsequently removed by distillation. The purpose of the present invention is to ensure removal of strongly acidic impurities, including low molecular weight sulfonic acids, prior to distillation in order to minimize color formation and further loss of product by cracking.

The anion exchange resins useful in the method of this invention include essentially all known basic resins of this type. For the most part, they are amine or quaternary ammonium resins typically containing such moieties as dimethylbenzylamino groups or corresponding methyl-caternized groups attached to a polymer chain. Amine resins are often preferred. Many suitable resins are commercially available. For the purpose of the invention, the quaternary ammonium resins are employed in the free base form; that is, the counterion therein is the hydroxide anion.

Contact between the mother liquor and the anion exchange resin may be effected by any convenient means. It is generally preferred to pass the mother liquor through a column containing the resin, at temperatures in the range of about 45°-125° C. and preferably about 50°-75° C. Passage of the mother liquor through the column may be upward or downward.

Upon contact with the anion exchange resin, acidic impurities are removed by salt formation therewith. When the resin has been exhausted, it may be regenerated by treatment with aqueous base. Such treatment is ordinarily preceded by washing with liquid phenol, to remove base-insoluble tarry impurities whose presence would decrease the efficiency of the resin.

It has been found that the method of this invention is essentially completely successful in suppressing decomposition of bisphenol A upon distillation of the mother liquor. Mother liquor streams in which product decomposition would occur to the extent of as high as 50% become completely stable during the distillation operation. Moreover, product color is substantially decreased.

The method of this invention is illustrated by the following examples.

EXAMPLE 1

Two different bisphenol A mother liquor streams were utilized. In order to determine the tendency of each stream to decompose, 163 grams thereof was distilled to a pot temperature of 210° C. An aliquot was removed and analyzed by high pressure liquid chromatography to determine the amount of bisphenol A present. The mixture was then heated under reflux for 4 hours and a second aliquot removed and similarly analyzed, and the percent cracking was determined by comparison of the results of the two analyses.

A 1-inch by 11-inch glass column equipped with a heated jacket was charged with 30 grams of each of four anion exchange resins in the free base form, identified as follows:

Resin 1—a polystyrene resin with benzyltrimethylammonium substituents.

Resin 2—a polystyrene backbone with benzyldimethylamine substituents.

Resins 3 and 4—two different acrylic backbone resins with benzyldimethylamine substituents.

A total of 1500 grams of mother liquor was passed upward through said columns at a weight-height space velocity of 6.7 hrs.$^{-1}$ and a temperature of 50° C. The results are listed in the following table.

| Resin | % cracking | |
|---|---|---|
| | Before treatment | After treatment |
| 1 | 14.7 | 0 |
| 2 | 34.6 | 0 |
| 3 | 14.7 | 0 |
| 4 | 14.7 | 0 |

EXAMPLE 2

A 6-pound sample of Resin 1, exhausted by mother liquor treatment according to Example 1, was washed with liquid phenol, water and 23 gallons of 6.5% aqueous sodium hydroxide solution, and then with deionized water until the pH of the effluent was neutral. The regenerated resin was employed as in Example 1 with a mother liquor which cracked to the extent of 48%. The effluent showed 0% cracking, and the regenerated resin had a lifetime identical to that of the original.

EXAMPLE 3

Melt color determinations according to ASTM procedure D1209 were made on two separate bisphenol A mother liquor streams, before and after passage through a column similar to that of Example 1. The following color results were obtained.

| Before | After |
|--------|-------|
| 280    | 200   |
| 260    | 200   |

We claim:

1. A method for recovering bisphenol A from a product stream which comprises:

forming and separating an adduct of bisphenol A and phenol, leaving a crude liquid stream containing crude bisphenol A and impurities;

removing acidic impuritites from said crude liquid stream by contact with a basic ion exchange resin at a temperature in the range of about 45°-125° C. for a period of time effective to remove said impurities by salt formation with said resin; and recovering further bisphenol A from the resin-treated crude liquid stream by distillation.

2. A method according to claim 1 wherein contact with the anion exchange resin is effected at a temperature in the range of about 50°-75° C.

3. A method according to claim 2 wherein said contact is effected by passing said crude liquid stream through a column containing said resin.

4. A method according to claim 3 which includes the step of regenerating said resin by treatment with aqueous base after said contact has been effected.

5. A method according to claim 2 wherein the anion exchange resin is an amine resin.

6. A method according to claim 2 wherein the anion exchange resin is a quaternary ammonium salt resin.

7. A method according to claim 4 wherein the aqueous base treatment is preceded by washing with liquid phenol.

8. A method according to claim 7 wherein the anion exchange resin is an amine resin.

9. A method according to claim 7 wherein the anion exchange resin is a quaternary ammonium salt resin.

* * * * *